United States Patent [19]
Karmarkar

[11] Patent Number: 5,567,307
[45] Date of Patent: Oct. 22, 1996

[54] SYSTEM AND A METHOD FOR USING A SMALL SUPPRESSOR COLUMN IN PERFORMING LIQUID CHROMATOGRAPHY

[75] Inventor: Shreekant V. Karmarkar, New Berlin, Wis.

[73] Assignee: Lachat Instruments, Milwaukee, Wis.

[21] Appl. No.: 316,641

[22] Filed: Sep. 30, 1994

[51] Int. Cl.$^6$ .................................................. B01D 15/08
[52] U.S. Cl. ........................................ 210/198.2; 210/656
[58] Field of Search .................................. 210/656, 659, 210/662, 198.2, 264; 422/70; 436/161

[56] References Cited

U.S. PATENT DOCUMENTS

| | | | |
|---|---|---|---|
| 3,920,397 | 11/1975 | Small et al. | 210/284 |
| 3,923,460 | 12/1975 | Parrott et al. | 210/656 |
| 3,925,019 | 12/1975 | Small et al. | 210/656 |
| 3,926,559 | 12/1975 | Stevens | 210/284 |
| 4,242,097 | 12/1980 | Rich, Jr. et al. | 210/198.2 |
| 4,314,823 | 2/1982 | Rich, Jr. et al. | 210/198.2 |
| 4,403,039 | 9/1983 | Ban et al. | 436/150 |
| 4,448,691 | 5/1984 | Davis | 210/635 |
| 4,459,357 | 7/1984 | Jansen et al. | 436/161 |
| 4,474,664 | 10/1984 | Stevens et al. | 210/656 |
| 4,549,965 | 10/1985 | Davis | 210/656 |
| 4,751,004 | 6/1988 | Stevens et al. | 210/659 |

FOREIGN PATENT DOCUMENTS

WO95/06246  3/1995  WIPO .......................... 210/198.2

OTHER PUBLICATIONS

Hollow Fiber Ion–Exchange Suppressor for Ion Chromatography, Anal. Chem. 1981, 53, pp. 1488–1492 Authors: Timothy S. Stevens, James C. Davis, Hamish Small.

VICI Valco Instruments Co., Inc. Catalog, 1993, Valco Instruments Co. Inc., Houston, Texas, a 12 page article.

*Determination of Trace Anions in Water by Multidimensional Chromatography*, Thomas B. Hoover and George D. Yager, Analytical Chemistry, vol. 56, No. 2, Feb. 1984, pp. 221, 223, & 225.

The Practice of Ion Chromatography, Frank C. Smith, Jr. and Richard C. Chang, John Wiley & Sons, 1983, pp. 18–19.

*Modern Inorganic Chromatography*, Hamish Small, Analytical Chemistry, vol. 55, No. 5, Feb. 1983, pp. 234, 236, 238, 240, & 242.

*Improve the Performance of Any Ion Chromatograph*, Alltech Everything for Chromatography Bulletin #284, Alltech Associates, Inc., 1983, a 4 page article.

*Matrix Elimination in Liquid Chromatography Using Heart–Cut Column Switching Techniques*, Analytical Chemistry, vol. 63, No. 14, Jul. 15, 1991, pp. 1362–1366.

Handbook of Ion Chromatography, Joachim Weiss, Chapter 8.2 The Chromatography Module, Dionex Corporation, 1986, pp. 179–180.

*Single–column ion chromatography aids rapid analysis*, T. H. Jupille, D. W. Togami and D. E. Burge, Industrial Research and Development, Feb. 1983, a six page article.

*Ion Chromatographic Analysis of Anions Using A Solid–Phase Chemical Suppressor*, Raaidah Saari–Nordhaus and James M. Anderson Jr., American Laboratory, Jan. 1994, a five page article.

(List continued on next page.)

Primary Examiner—Ernest G. Therkorn
Attorney, Agent, or Firm—Foley & Lardner

[57] ABSTRACT

A method and a system for ion chromatography are disclosed. The system includes a small capacity suppressor column for suppressing the conductivity of the eluant carrying the ionic species being tested. The size of the suppressor column permits regeneration of the suppressor column between each sample tested to provide accurate and precise test results for every sample. The method permits regeneration of the suppressor column during the loading of each sequential sample to prevent impairment to productivity.

10 Claims, 6 Drawing Sheets

OTHER PUBLICATIONS

*Separation of Sulfite, Sulfate and Thiosulfate by Ion Chromatography with Gradient Elution* by Thomas Suden, Mats Lindgren, Anders Cedergren and Harry D. Siemer, Analytical Chemistry, vol. 55, No. 1, Jan. 1983, pp. 2–4.

*Solid Phase Chemical Suppression for Ion Chromatographic Analysis of Anions* by Raaidah Saari–Nordhaus and James M. Anderson, Jr., The Pittsburgh Conference, Georgia World Congress Center, Atlanta Georgia, Mar. 8–12, 1993, Abstracts, one page submitted.

*Ion Chromatography*, Hamish Small, Modern Analytical Chemistry, Plenum Press, 1989, pp. 158, 159, 164, 165–167, & 170–171.

*Ion Chromatography*, Chromatographic Methods, Douglas T. Gjerde and James S. Fritz, Dr. Alfred Hothig Verlag Heidelberg, 1987 pp. 102–103.

*Ion Chromatography*, John C. MacDonald, American Laboratory, Jan. 1979, pp. 45–54.

The Pittsburgh Conference, Georgia World Congress Center, Atlanta, Georgia, Mar. 8–12, 1993, Abstracts, two pages submitted.

Snyder, Introduction to Modern Liquid Chromatography, John Wiley & Sons, 1979, pp. 103–117.

SYSTEM AND A METHOD FOR USING A SMALL SUPPRESSOR COLUMN IN PERFORMING LIQUID CHROMATOGRAPHY

FIELD OF THE INVENTION

This invention relates generally to a system and a method for performing liquid chromatography, and particularly to an ion chromatography method and system that uses a small suppressor column to enhance signal to noise ratio and to obtain accurate and precise results.

BACKGROUND OF THE INVENTION

Ion chromatography (IC) is often used to test for organic and inorganic ions in various sample materials, including waste water, lake water, underground water, process streams, air samples, and food products. Generally, two ion exchange columns, often called a guard column and an analytical column, are used in series. An eluant, commonly referred to as the mobile phase, carries the sample to be tested through the ion exchange columns. The analytical column effluent is then allowed to go through a suppressor column and finally through an electrical conductivity detector. The analytical column separates the ions from the remainder of the injected sample, and the suppressor column suppresses the conductance of the eluant, while promoting the conductance of the separated ions. Typically, the suppressor column is filled with an ion exchange resin that suppresses the conductivity of the eluant electrolyte. The analytical column and the suppressor column can be designed to test for either anions or cations. Usually, the eluant constitutes an electrolyte, such as dilute base or acid in deionized water.

The conventional IC system described above suffers from several drawbacks. Periodically, the suppressor column must be regenerated or replaced, because the ion exchange resin gradually loses its functioning ability. For instance, in the case of IC for anions, the reaction shown below eventually converts all of the ion-exchange sites in the suppressor column in the $H^+$ form to the $Na^+$ form, causing the suppressor column to lose its ability to capture $Na^+$ from the eluant (a mixture of $NaHCO_3$ and $Na_2CO_3$):

As the reaction shown above proceeds, the background conductance of the eluant drifts upward and, at the same time, signal enhancement for the analyte is lowered, resulting in poor precision for determination of various ionic species. Additionally, in many applications of chromatographic analysis, a phenomenon referred to as a "water dip" occurs and is represented on the graphic output by a negative peak as compared to the positive peaks of the various ionic species. As the resin material in the suppressor column deteriorates, this negative peak shifts towards the first positive peak, e.g., fluoride, and can actually overlap the positive peak. This makes interpretation of the graphic output more difficult and adversely affects accuracy and precision. Also, it usually takes 8–10 hours to complete regeneration of an exhausted suppressor column, resulting in impairment to productivity.

Additionally, many existing suppressor columns have substantial internal dead space that leads to band broadening, rendering it difficult to accurately determine the ionic species within the samples being tested. Band broadening can be limited by using somewhat smaller suppressor columns with less dead space, but the industry has had limited success with the smaller suppressor columns because they require frequent regeneration. Thus, the testing of samples is constantly interrupted while the suppressor column is either replaced or regenerated. Attempts also have been made to reduce the frequency of regeneration by providing a relatively low capacity for exchange in the analytical column, but this is problematic because the analytical column capacity can be overloaded and resolution between the ionic species is reduced.

The determination of weak-acid or weak-base ions using a suppressor column is complicated by ion-exclusion effects in the unexhausted portion of the column. For instance, taking an example of a weak-acid anion such as nitrite, the peak height for a known $NO_2$ concentration is smaller when the suppressor column is unexhausted than that when the suppressor column is exhausted. As the suppressor column becomes exhausted, the ion-exclusion effects decrease, resulting in increased peak height.

The present invention eliminates the various drawbacks of existing methods and devices for performing suppressed ion chromatography.

SUMMARY OF THE INVENTION

The present invention is directed to a novel suppressor column and a novel method for performing ion chromatography in which the suppressor column is regenerated frequently and quickly. According to a preferred embodiment, the invention involves a method for performing liquid chromatography of ionic species. The method comprises the steps of providing an eluant and sequentially injecting liquid samples into the eluant, each liquid sample having certain ionic species. The method further includes the step of separating at least one ion from each liquid sample. The at least one ion and its corresponding eluant is then directed through a suppressor column where the conductivity of the eluant is suppressed. The suppressor column is regenerated between each sequential sample to provide consistent suppression of conductivity. The invention thus provides a consistent chromatographic performance from sample to sample, without loss of productivity.

According to another aspect of the invention, a system is provided for consistently performing liquid chromatography of ionic species. The system includes a transport assembly adapted to transport an eluant. A sample injector is connected to the transport assembly and includes a valve to selectively permit introduction of a plurality of sequential samples into the eluant, where each sample contains at least one ionic species. The system also includes an analytical column connected to the transport assembly and disposed to receive the plurality of sequential samples and eluant therethrough. In the analytical column, at least one ionic species is separated from each sample.

A suppressor column is connected to the transport assembly downstream from the analytical column and is adapted to suppress the electrical conductivity of the eluant. A regeneration assembly cooperates with the suppressor column to supply regenerant through the suppressor column. This flow of regenerant through the suppressor column is controlled by a valve assembly that also controls the flow of eluant and the ionic species through the suppressor column. Preferably, the valve is appropriately timed to permit a flow of regenerant through the suppressor column between the introduction of each sample into the eluant.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

Figure 1:
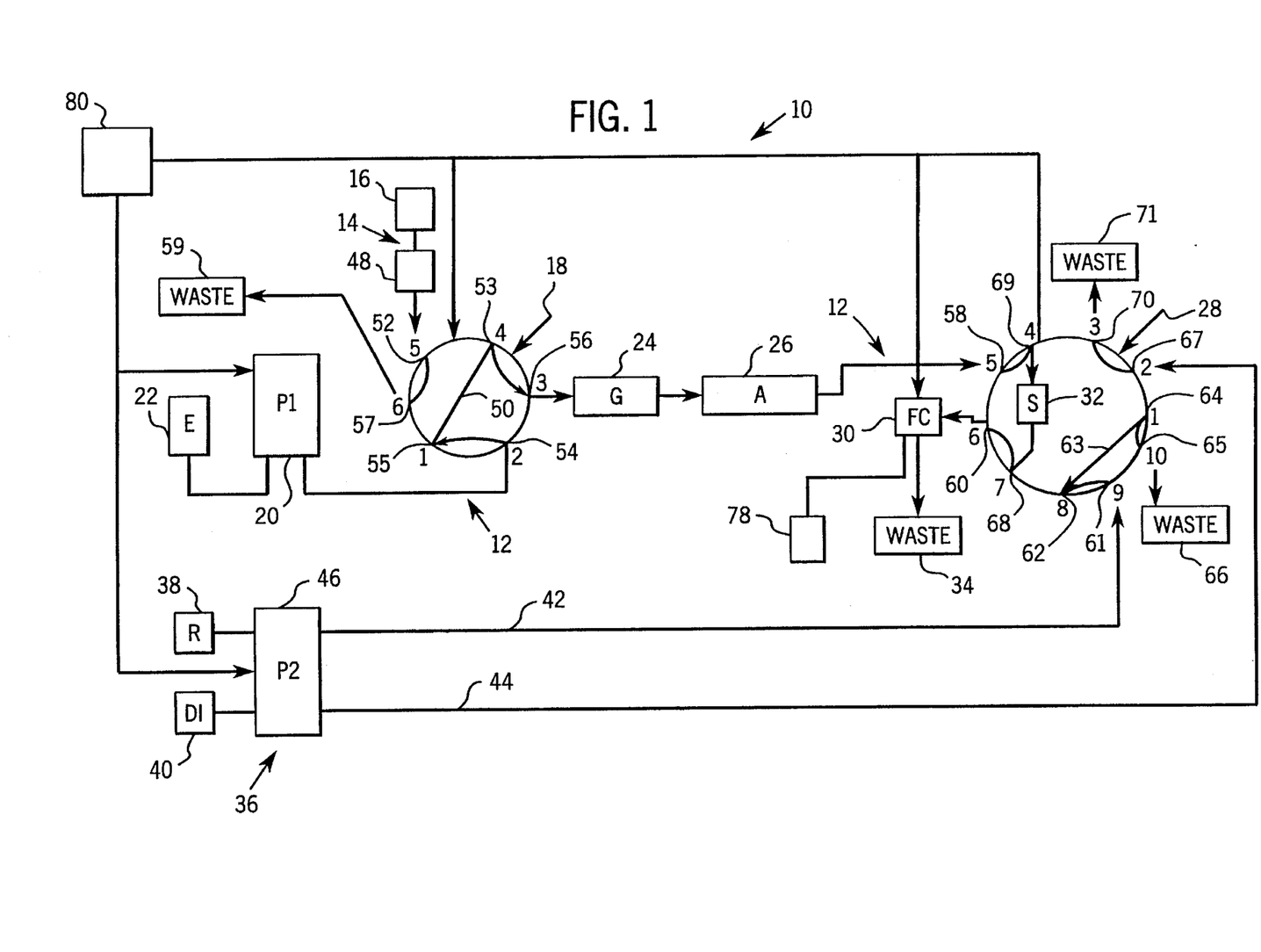
FIG. 1 is a schematic representation of the ion chromatography system according to a preferred form of the invention showing the fluid flow paths during testing of a sample.

Referring generally to FIG. 1, an ion chromatography system 10 includes a transport assembly 12, e.g. conduits or tubing, for transporting an eluant. System 10 further includes a sample injector 14 having a sample supplier 16, such as an XYZ sampler, Model No. AIM1250, supplied by Lachat Instruments, and a valve 18.

Valve 18 is preferably a multi-port valve connected in line with transport assembly 12 to receive eluant supplied by a pump 20 connected between valve 18 and an eluant source 22. A guard column 24 is connected to transport assembly 12 downstream of valve 18. Similarly, an analytical column 26 is connected to transport assembly 12 downstream from guard column 24.

A multiport valve 28 is connected to transport assembly 12 downstream from analytical column 26 to conduct fluid flow to a variety of locations. A detector 30, such as a conductivity detector, is connected downstream from multiport valve 28, and a suppressor column 32 is connected between two ports of multiport valve 28. Valve 28 may be controlled to selectively permit effluent flow from suppressor column 32 to conductivity detector 30 prior to entering a waste receptacle 34.

A regeneration assembly 36 is also connected to multiport valve 28. Regeneration assembly 36 includes a regenerant source 38 and a deionized water source 40. Regenerant and deionized water are supplied to multiport valve 28 by a regenerant supply line 42 and a deionized water supply line 44, respectively. Preferably, a pump 46, such as a peristaltic pump, moves both regenerant and deionized water through their respective supply lines to multiport valve 28.

Figure 2:
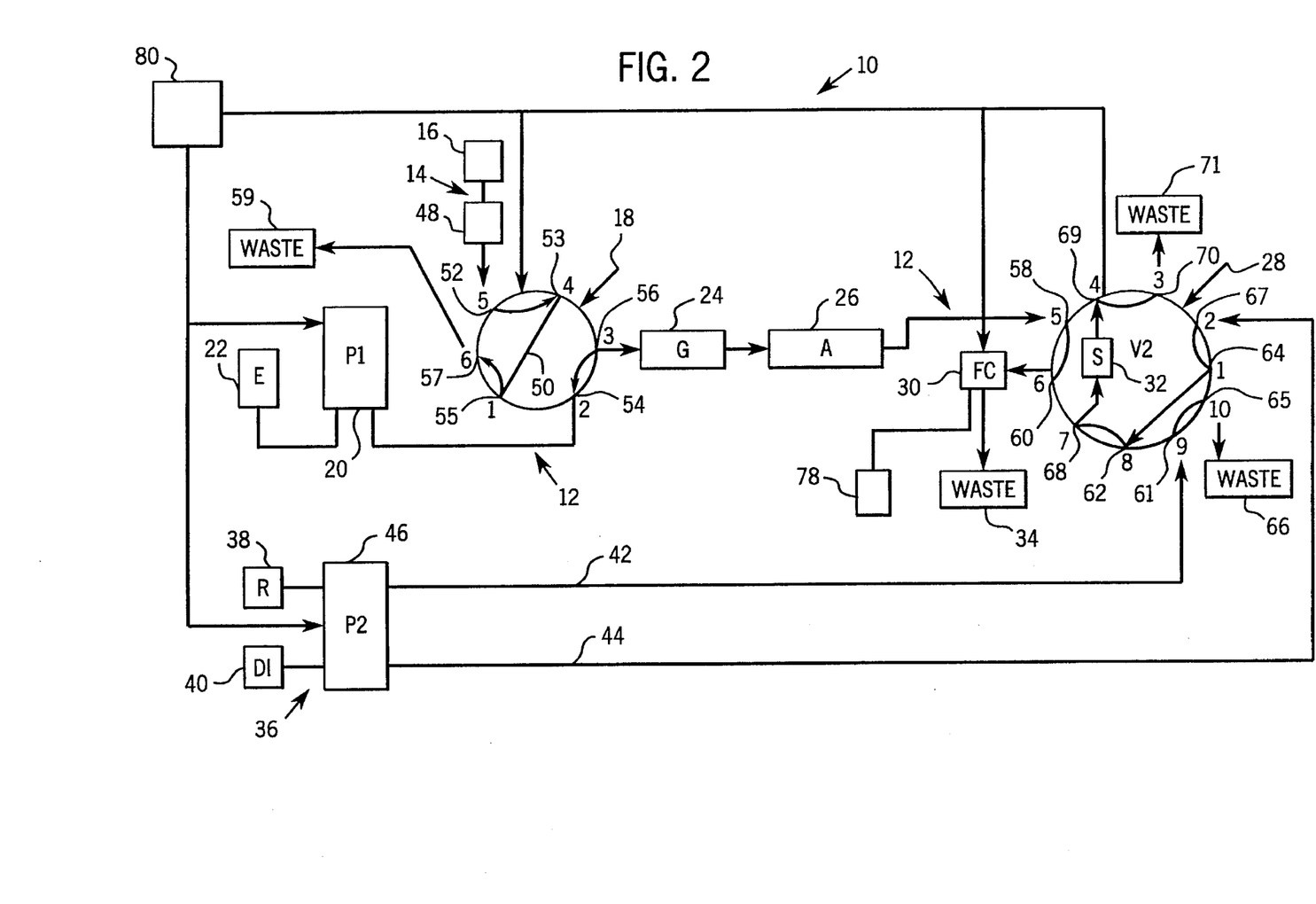
FIG. 2 is a schematic representation of the ion chromatography system of FIG. 1 showing the fluid flow paths during loading of a sample.

In operation, sample supplier 16 may include a variety of samples that are sequentially processed and tested in ion chromatography system 10. The samples are sequentially pumped by a sample supply pump 48 to a reservoir 50, such as a coiled piece of tubing. As shown in FIG. 2, during loading of a sample in reservoir 50, the sample is supplied to a first port 52 of valve 18 that permits flow of the sample through a port 53 and into reservoir 50. However, the sample is not permitted to flow from valve 18 to guard column 24 during loading, but a portion of the sample flows past a port 55 and exits valve 18 through a port 57 before entering a waste receptacle 59. Simultaneously, eluant is pumped to a port 54 of valve 18 and permitted to flow out of a port 56 and into guard column 24. The eluant flows through guard column 24, analytical column 26, and into an inlet port 58 of multiport valve 28. Then the eluant flows through multiport valve 28 and exits through an exit port 60, where it continues to flow through conductivity detector 30 and empties into waste receptacle 34.

Meanwhile, the suppressor column 32 is regenerated. Prior to loading, regenerant fluid is supplied by pump 46 from regenerant source 38 to a regenerant inlet port 61 which, in turn, is connected to a port 62 (see FIG. 1). A regenerant reservoir 63 is connected between port 62 and a port 64 which, in turn, is connected to a regenerant exit port 65 that leads to a waste receptacle 66. Thus, a sample of regenerant is captured in reservoir 63 prior to shifting multiport valve 28 to the load position as illustrated in FIG. 2.

In this load position, deionized water flows from source 40 via pump 46 to enter value 28 at a port 67. The deionized water flows from port 67 to port 64 and forces the regenerant through reservoir 63 past port 62 and to a port 68 of valve 28. Suppressor column 32 is connected between port 68 and a port 69. Thus, the deionized water forces the regenerant sample through the suppressor column 32 and then flushes the remaining regenerant fluid from suppressor column 32 prior to passing through a waste port 70 and into a waste receptacle 71. During this time, the regenerant is flowing into port 61 and out of port 65 to waste receptacle 66. It should be noted that waste receptacles 34, 66, and 71 can be individual receptacles or a combined receptacle for receiving waste fluids.

In the preferred embodiment, the flow of regenerant and deionized water through suppressor column 32 occurs during the loading of a sample in reservoir 50. To avoid downtime while suppressor column 32 is regenerated, it is preferred that the total time allotted for flow of regenerant and deionized water through suppressor column 32 be limited to less that two minutes. In actual practice, it has been determined that a flow period of approximately 72 seconds is sufficient to prepare suppressor column 32 for receipt of the next test sample. It has also been determined that approximately 33% of the flow period can be used for flow of regenerant, while the other 67% can be used for flow of deionized water. The flow period and ratio of regenerant flow time to deionized water flow time can, however, be adjusted according to the sample types and the components of ion chromatography system 10.

After the sample is loaded in reservoir 50 and the regenerant and deionized water have passed through suppressor column 32, the loaded sample is ready to be tested. As shown in FIG. 1, valve 18 is repositioned to permit the eluant to flow through port 54 and past port 55, where the sample is mixed or injected into the eluant in reservoir 50. The mixture of sample and eluant continues to flow past port 53 and exits through port 56 into transport assembly 12. The mixture then flows into guard column 24, which prohibits particulates or impurities that may reside in the sample from getting into the analytical column 26, and also effectively begins to separate the ionic species.

Next, the sample and eluant mixture flow through analytical column 26 where the ionic species are further separated from the rest of the sample prior to entering inlet port 58 of multiport valve 28. The mixture then flows to suppressor column inlet port 69 and through suppressor column 32 where the conductance of the eluant is suppressed. After suppressor column 32, the eluant and sample mixture pass through port 68 and then flow to conductivity detector 30 through exit port 60. Conductivity detector 30 measures the conductivity of the various ionic species separated from the sample and outputs this analog data to an A/D conversion device 78, such as an Omnion IC data station, that also provides a graphical representation of the conductance of the various ionic species.

During processing of the sample, regenerant is flowing through multiport valve 28 and regenerant reservoir 63 to waste receptacle 66, and deionized water is flowing through multiport valve 28 to waste receptacle 71. Thus, as soon as the testing of the sample is completed, regenerant reservoir 63 has been filled and multiport valve 28 can be repositioned to permit regeneration of suppressor column 32, while the next sample is loaded in reservoir 50.

Figure 3:
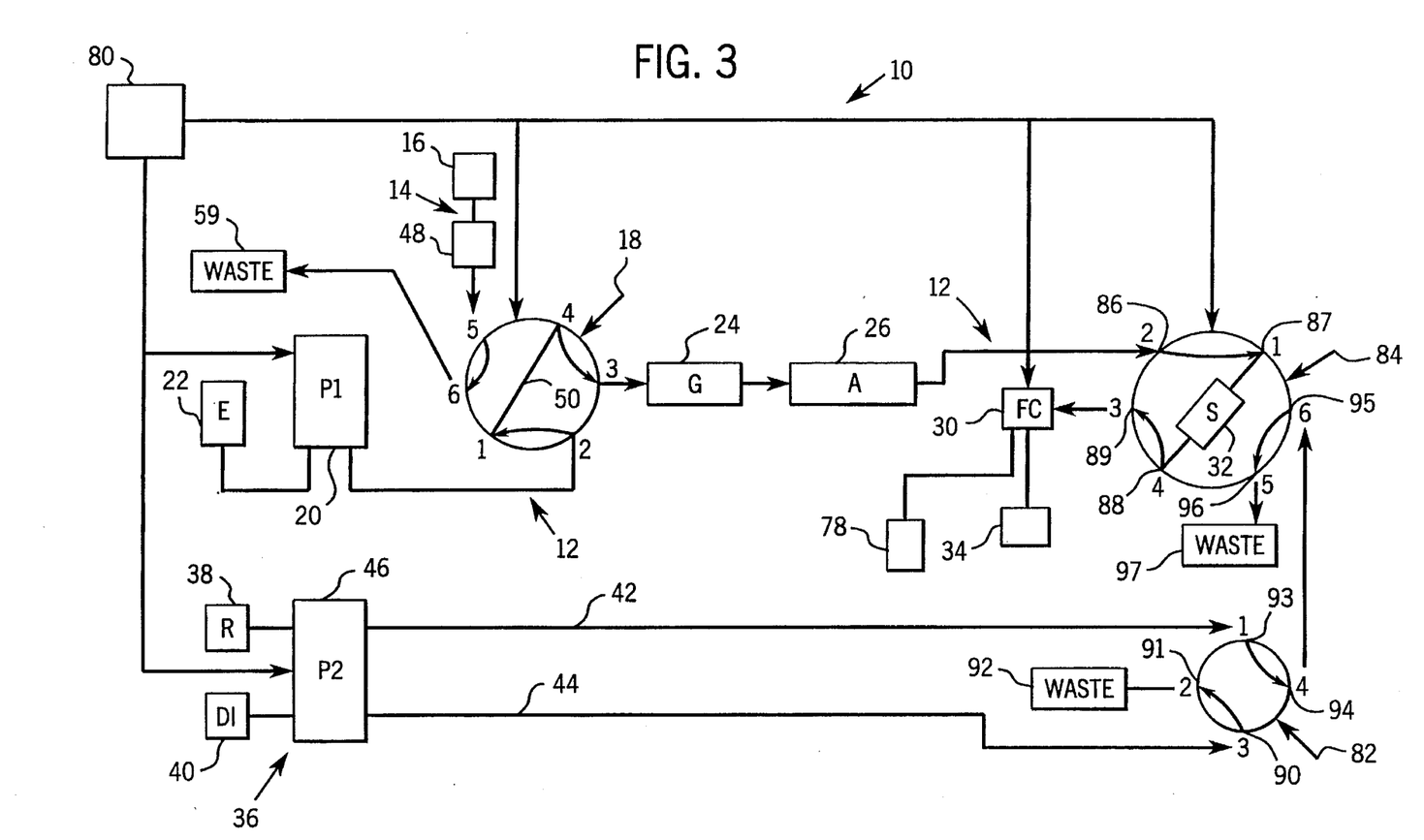
FIG. 3 is a schematic representation of an alternate embodiment of the ion chromatography system of FIG. 1 in an inject state.
Figure 4:
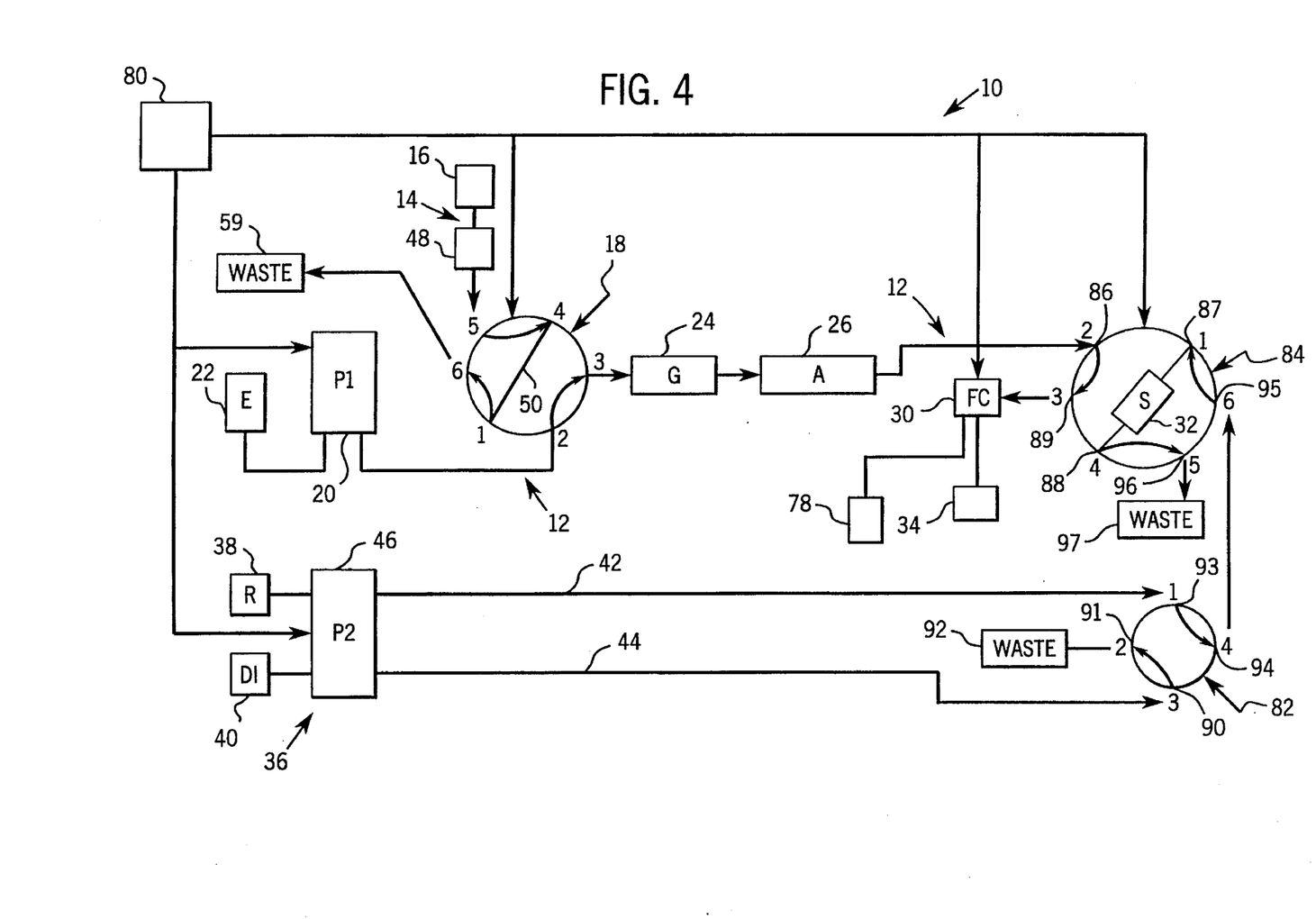
FIG. 4 is a schematic representation of the alternate embodiment in a first load state.
Figure 5:
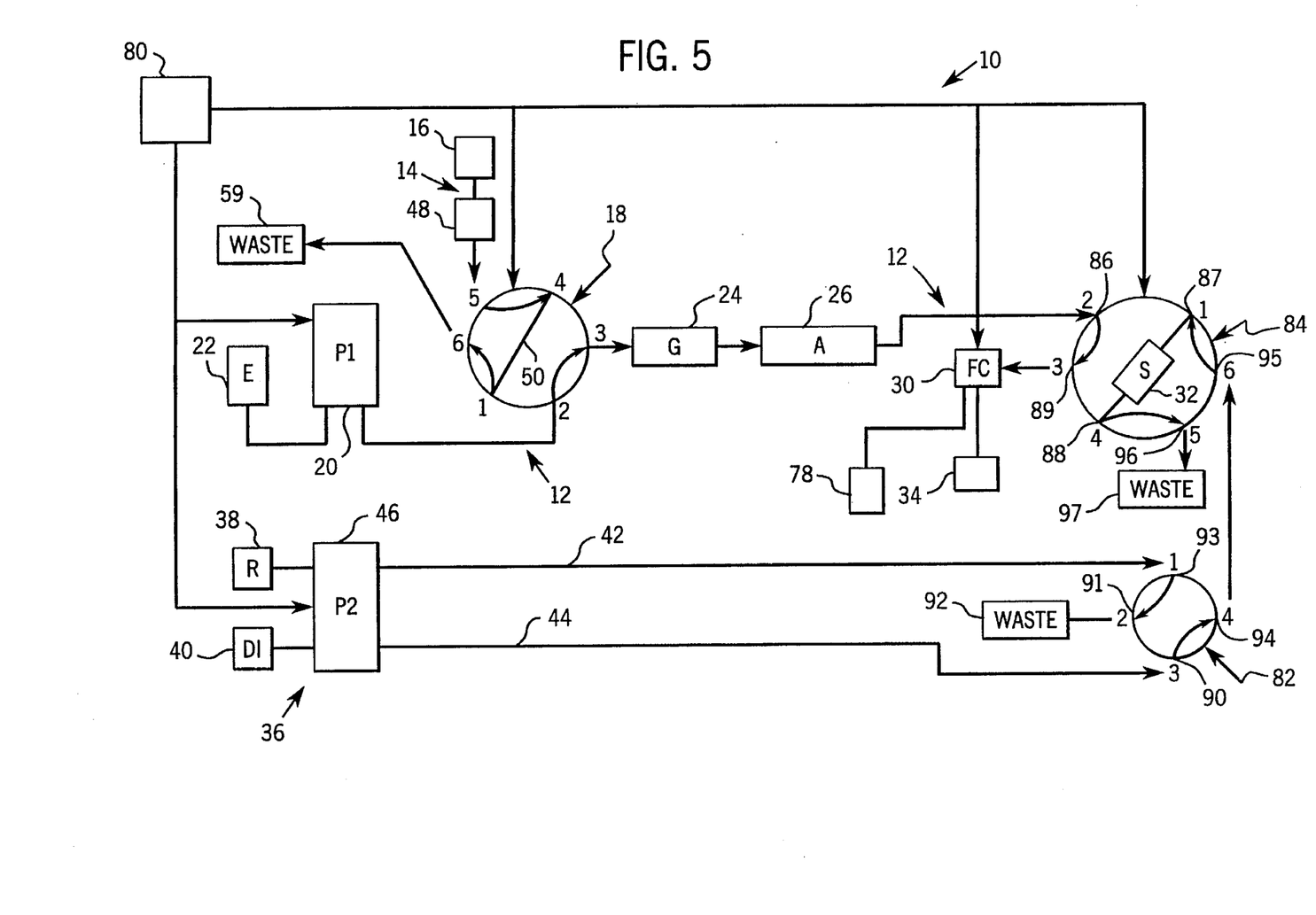
FIG. 5 is a schematic representation of the alternate embodiment in a second load state.

Ion chromatography system 10 may have a variety of components arranged in a variety of configurations. For example, various multiport valves or combinations of multiport valves can be used; a variety of guard columns and analytical columns can be used; various pumps are available to transfer the fluids; and, of course, different samples, eluants, and regenerants are available for various analytical procedures, including the detection of both anions and cations. Another possible valve configuration is also shown in FIGS. 3–5 and described below, wherein a combination of 6-port and 4-port valves is used to regenerate the suppressor column while the sample is being loaded.

The following list of available components are provided as an example of a typical combination. Eluant pump 20 may be a high pressure pump, Model No. Series III, supplied by Lachat Instruments, regenerant and deionized water pump 46 may be a peristaltic pump, Model No. 302SL, supplied by Lachat Instruments, and supply pump 48 may be a peristaltic pump, Model No. 302SL, supplied by Lachat Instruments. Similarly, valves 18 and 28 may comprise a variety of valves, but preferably valve 18 is a six port valve, such as the Model 9010 manufactured by Rheodyne and multiport valve 28 is a ten port valve, such as Model 7610-601 manufactured by Rheodyne. Suitable guard columns 24 and analytical columns 26 for processing samples having anions are the anion guard column supplied by Lachat Instruments and the analytical column EPA 300A Anion Profiling Column supplied by Lachat Instruments. Other guard columns and analytical columns are available for use with cation detection. Also, the actuation of the various pumps and valves may be controlled by a microprocessor, and preferably by a computer 80, such as the SS-420 supplied by Lachat Instruments.

The suppressor column 32 has a low interior volume to lessen band broadening and to permit quick regeneration prior to the analysis of each sample. Preferably, the entire regeneration process takes place during the loading of the next sequential test sample. In the preferred embodiment, suppressor column 32 is less than 40 millimeters in length and has a hollow, cylindrical interior with an inside diameter of ten millimeters or less. In the most preferred embodiment, the internal length of the suppressor column is approximately 20 millimeters, while the inside diameter of the column is approximately 4.6 millimeters. The shape, configuration, and internal capacity of suppressor column 32 may be adjusted for the particular application, but it is important for the internal volume to be sufficiently limited to permit regeneration between each sequential sample. When suppressor column 32 is employed in the determination of anions in a given sample, it is preferably filled with a particulate-type resin material, such as Dowex 50WX-12 in $H^+$ form. However, if suppressor column 32 is used to help determine cations in a given sample, the internal resin is preferably a particulate-type material, such as Dowex 1X–12 in OH form.

EXAMPLE

The following is an example of how ion chromatography system 10 can be used to determine the ionic species within given samples. In this example, the samples contain at least one and possibly a mixture of seven common inorganic anions including fluoride, chloride, nitrite, bromide, nitrate, phosphate, and sulfate (see FIG. 6). In the first sample supplied by sample supplier 16 and loaded into reservoir 50, there is at least a component of fluoride to undergo ion chromatography.

The eluant supplied from eluant source 22 includes a mixture of sodium carbonate and sodium bicarbonate which mixes with the subject sample at valve 18. The combination of sample and eluant passes through guard column 24 which assists in removing particles and impurities from the mixture. As the sample and eluant pass through analytical column 26, the fluoride ion is eluted from the sample and passed along with the eluant through suppressor column 32. While in analytical column 26, the eluant is at least partially broken in to its ionic components, e g $Na^+$, $HCO_3^-$, and $CO_3^{2-}$.

Figure 6:
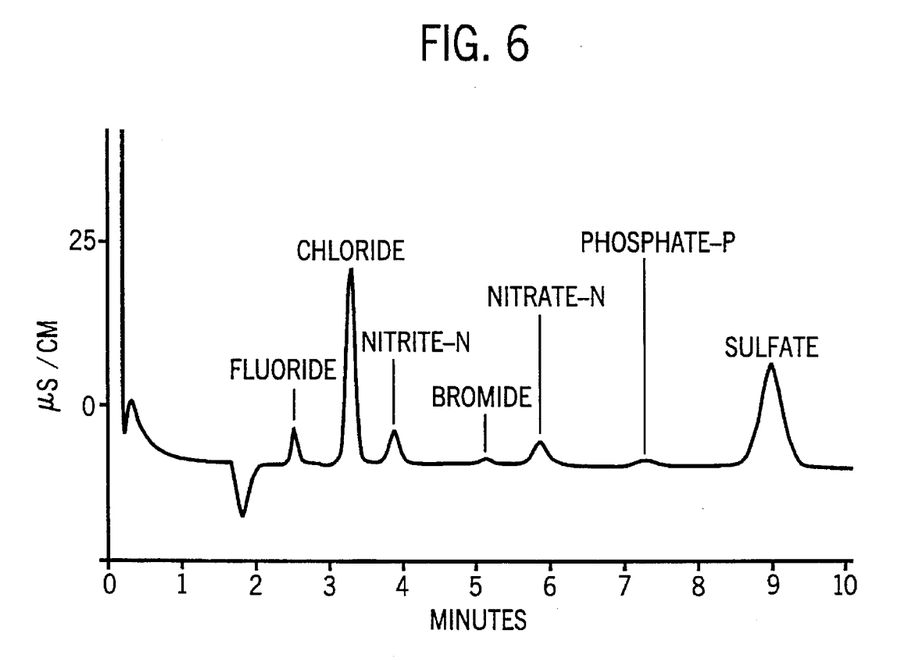
FIG. 6 is a graphic representation of the conductivity of typical ionic species within a test sample.

The eluted fluoride ion combines with the sodium ion and travels to suppressor column 32 which is preferably packed with high-exchange capacity cation exchange particles in $H^+$ form. As the analytical column effluent travels through suppressor column 32, the eluant is converted into carbonic acid which has minimal conductance. Simultaneously, the fluoride is converted from its $Na^+$ form to $H^+$ form which results in an increased signal for the anionic species, providing a greater signal to background noise ratio. Thus, the fluoride ion can readily be detected by detector 30 and converted to a graphic representation by conversion device 78 as shown in FIG. 6. This same analysis can be conducted for the other anions represented in the graph of FIG. 6.

After the sample passes through suppressor column 32 and during loading of the next sequential sample in reservoir 50, suppressor column 32 is regenerated. Regeneration is accomplished by first passing sulfuric acid through suppressor column 32 in a reverse flow direction for approximately 24 seconds. Then, the deionized water following the regenerant is similarly directed in a reverse flow through suppressor column 32 for approximately 48 seconds to prepare suppressor column 32 for the next sample. Meanwhile, the next sequential sample has filled reservoir 50 and valves 18 and 28 are simultaneously repositioned to permit the analysis of this next sequential sample. By controlling valve 18 and multiport value 28, sequential samples are consistently analyzed by ion chromatography system 10, and suppressor column 32 is regenerated continuously while each sequential sample is loaded into reservoir 50. Thus, there is no chance for deterioration of suppressor column 32, and the output of conductivity detector 30 and conversion device 78 remains consistent and accurate for all of the samples.

In the alternate embodiment illustrated in FIGS. 3–5, the overall system is the same as that described above, except for replacement of the ten port valves 28 with a pair of valves including a four port valve 82 that interacts with a six port valve 84. In this embodiment, during the inject state when the sample is being analyzed, eluant carrying the ionic species enters six port valve 84 through an inlet port 86 that directs the mixture to a port 87. Suppressor column 32 is connected between port 87 and a port 88 which, in turn, is connected to an exit port 89 that leads to conductivity detector 30. During the testing of the sample, deionized water flows into a port 90 of four port valve 82 and out of a port 91 into a waste receptacle 92. Meanwhile, regenerant flows into a port 93 of four port valve 82 and out through a port 94 that is connected to a port 95 of six port valve 84. The regenerant flows into port 95 and exits through a port 96 into a waste receptacle 97 as shown in FIG. 3.

After testing of the sample is completed, valve 18 and six port valve 84 are shifted to a different position for regeneration of suppressor column 32 as shown in FIG. 4. In this configuration, regenerant enters six port valve 84 through port 95 and travels to port 87 where it is directed through suppressor column 32. As the regenerant exits suppressor column 32, it travels past port 88 and exits through port 96 to waste receptacle 97.

After sufficient regenerant, e.g. 2 milliliters, has passed through suppressor column 32, four port valve 82 shifts to another position as shown in FIG. 5 so the regenerant entering port 93 is directed through port 91 and into waste receptacle 92. Simultaneously, the deionized water is directed from inlet port 90 through port 94 which is connected to port 95 of six port valve 84. The deionized water is then directed through the same path as the regenerant to flush the system as illustrated in FIG. 5. In other words, the deionized water travels past port 87, through suppressor column 32, past port 88, and exits port 96 into waste receptacle 97. During this regeneration process, the next sequential sample to be tested has been loaded into reservoir 50. Thus, the combination of the six port valve 84 and four port valve 82 effectively functions the same as 10 port valve 28 and allows the suppressor column to be completely regenerated between each sequential sample.

It will be understood that the foregoing description is of a preferred exemplary embodiment of this invention and that the invention is not limited to the specific form shown. For example, various pumps and valves may be combined in a variety of configurations, the guard column, analytical column, and suppressor column may contain various internal materials depending on the type of sample to be analyzed, and the times allotted for loading of samples and regeneration of the suppressor column may be adjusted according to the particular type of samples tested. These and other modifications may be made in the design and arrangement of the elements without departing from the scope of the invention as expressed in the appended claims.

What is claimed is:

1. A system for consistently performing liquid chromatography of ionic species, comprising:

a transport assembly adapted to transport an eluant;

a sample portion injector including a valve connected to the transport assembly to selectively permit introduction of a plurality of sequential sample portions into the eluant, each sample portion containing at least one ionic species;

an analytical column connected to the transport assembly and disposed to receive the plurality of sequential sample portion and eluant therethrough, wherein the at least one ionic species is separated from the sample portion;

a suppressor column connected to the transport assembly downstream from the analytical column, wherein the suppressor column suppresses the electrical conductivity of the eluant;

a regeneration assembly cooperating with the suppressor column to supply regenerant through the suppressor column, the regeneration assembly including a regenerant reservoir configured to receive a portion of regenerant;

a deionized water delivery system to deliver deionized water to the suppressor column; and a valve assembly which controls the flow of the regenerant, the deionized water, the eluant, and the at least one ionic species through the suppressor column, wherein the valve assembly is automatically actuable to selectively provide fluid communication between the regenerant reservoir and the suppressor column to direct a flow of the portion of regenerant through the suppressor column between the introduction of each sample into the eluant, further wherein the valve assembly is actuable to direct the deionized water through the regenerant reservoir to force the portion of regenerant out of the regenerant reservoir and into the suppressor column.

2. The system as recited in claim 1, further comprising a detector connected to the transport assembly to receive the eluant and the at least one ionic species.

3. The system as recited in claim 2, wherein the suppressor column has a flow length less than approximately 50 millimeters.

4. The system as recited in claim 3, wherein the suppressor column has a flow length less than approximately 25 millimeters.

5. The system as recited in claim 4, wherein the suppressor column is generally cylindrical and has an inside diameter less than approximately 10 millimeters.

6. The system as recited in claim 2, wherein the regeneration assembly includes a first pump to provide a flow of regenerant through the suppressor column and a second pump to provide a flow of deionized water through the suppressor column following the flow of regenerant.

7. The system as recited in claim 6, wherein the total flow time for both the regenerant and the deionized water is less that 120 seconds.

8. The system as recited in claim 7, wherein the total flow time for both the regenerant and the deionized water is less than 80 seconds.

9. A system for use in liquid chromatography where an eluant is sequentially injected with a plurality of test samples containing a group of ionic species, the group of ionic species being separated out of each sample and carried by the eluant to a detector which detects the conductivity of each ionic species in the group, the system comprising:

a reservoir configured to receive a test portion from one of the plurality of test samples;

a multiport valve having a first operational position, and a second operational position;

a suppressor column connected to the multiport valve;

a regenerator assembly connected to the multiport valve, to supply a regenerant to the suppressor column; and a deionized water delivery system connected to the multiport valve;

wherein the multiport valve alternates between the first operational position and the second operational position, the alternating of the multiport valve being controlled to permit the flow of the eluant combined with the one group of ionic species through the suppressor column to the detector in the first operational position and to permit flow of regenerant through the suppressor column between sequential groups of ionic species in the second operational position, further wherein the multiport valve is operational to direct the deionized water through the suppressor column following the flow of the regenerant through the suppressor column and the reservoir is filled with a second portion from the next sequential test sample when the multiport valve is in the second operational position.

10. The suppressor column assembly as recited in claim 9, wherein the suppressor column has a flow path less than approximately 40 millimeters in length.

\* \* \* \* \*